(12) United States Patent
Fu et al.

(10) Patent No.: US 10,874,533 B2
(45) Date of Patent: Dec. 29, 2020

(54) PLASTIC COVERED STENT FOR AORTIC DISSECTION AND AORTIC DISSECTION STENT

(71) Applicant: HANGZHOU WEIQIANG MEDICAL TECHNOLOGY CO., LTD., Hangzhou (CN)

(72) Inventors: Weiguo Fu, Hangzhou (CN); Yongsheng Wang, Hangzhou (CN); Jianmin Li, Hangzhou (CN); Tingchao Zhang, Hangzhou (CN)

(73) Assignee: HANGZHOU WEIQIANG MEDICAL TECHNOLOGY CO., LTD., Hangzhou (CN)

( * ) Notice: Subject to any disclaimer, the term of this patent is extended or adjusted under 35 U.S.C. 154(b) by 94 days.

(21) Appl. No.: 16/084,268

(22) PCT Filed: Mar. 16, 2017

(86) PCT No.: PCT/CN2017/076943
§ 371 (c)(1),
(2) Date: Sep. 12, 2018

(87) PCT Pub. No.: WO2017/157321
PCT Pub. Date: Sep. 21, 2017

(65) Prior Publication Data
US 2019/0070025 A1 Mar. 7, 2019

(30) Foreign Application Priority Data
Mar. 18, 2016 (CN) .......................... 2016 1 0158364

(51) Int. Cl.
*A61F 2/07* (2013.01)
*A61F 2/852* (2013.01)
(Continued)

(52) U.S. Cl.
CPC ................ *A61F 2/852* (2013.01); *A61F 2/07* (2013.01); *A61F 2/89* (2013.01);
(Continued)

(58) Field of Classification Search
CPC .... A61F 2/07; A61F 2220/0075; A61F 2/852; A61F 2002/828; A61F 2002/91508
See application file for complete search history.

(56) References Cited

U.S. PATENT DOCUMENTS

2008/0114441 A1 * 5/2008 Rust .......................... A61F 2/07
623/1.13
2009/0163951 A1 6/2009 Simmons
(Continued)

FOREIGN PATENT DOCUMENTS

CN 2724662 Y 9/2005
CN 101912319 A 12/2010
(Continued)

OTHER PUBLICATIONS

European Search Report for corresponding European patent application No. 17765863.0, dated Oct. 17, 2019.
(Continued)

*Primary Examiner* — Brian E Pellegrino
(74) *Attorney, Agent, or Firm* — Cooper Legal Group, LLC

(57) ABSTRACT

A plastic covered stent for aortic dissection and an aortic dissection stent are disclosed. The plastic covered stent for aortic dissection includes a tubular membrane and multiple annular stents sequentially sutured on the membrane along an axial direction. Part of the annular stents on the membrane are semi-suture stents. Each semi-suture stent has non-suture zones separable from the membrane. When the plastic covered stent is bent, the membrane corresponding to the non-suture zones at an inner bending side of the plastic
(Continued)

covered stent is separated from the semi-suture stents and folded inwardly. The semi-suture stents are distributed on a bending portion of the plastic covered stent for aortic dissection after being implanted.

12 Claims, 7 Drawing Sheets

(51) Int. Cl.
  *A61F 2/915* (2013.01)
  *A61F 2/89* (2013.01)
  *A61F 2/82* (2013.01)
(52) U.S. Cl.
  CPC ... *A61F 2002/075* (2013.01); *A61F 2002/828* (2013.01); *A61F 2002/91508* (2013.01); *A61F 2002/91525* (2013.01); *A61F 2210/0014* (2013.01); *A61F 2220/0075* (2013.01)

(56) References Cited

U.S. PATENT DOCUMENTS

2009/0171443 A1 7/2009 Kuppurathanam et al.
2013/0289700 A1 10/2013 Acosta-Acevedo

FOREIGN PATENT DOCUMENTS

| CN | 102100587 A | 6/2011 |
| CN | 102100587 B | 10/2013 |
| CN | 104027187 A | 9/2014 |
| CN | 205612591 U | 10/2016 |
| DE | 102011111223 A1 | 5/2014 |
| EP | 1759669 A1 | 3/2007 |

OTHER PUBLICATIONS

International search report issued in corresponding international application No. PCT/CN2017/076943 dated Jun. 19, 2017.

* cited by examiner

PLASTIC COVERED STENT FOR AORTIC DISSECTION AND AORTIC DISSECTION STENT

TECHNICAL FIELD

The present disclosure relates to the technical field of medical instrument, and particularly to a plastic covered stent for aortic dissection and an aortic dissection stent.

BACKGROUND

Aortic diseases mainly include aortic aneurysm and aortic dissection.

The aortic aneurysm is not real tumor, but pathologic aortic changes of local or general aortic dilation, caused by various reasons, with an aortic diameter 50% greater than a normal aortic diameter. The aortic aneurysm is further classified into aortic true aneurysm and aortic false aneurysm. The aortic true aneurysm is aortic aneurysm caused by pathologic enlargement or bulging of full thickness of aorta wall and aortic aneurysm wall. The aortic false aneurysm is hematoma formed by blood leaking from a tear of a torn or ruptured arterial wall and confined by tissue adjacent to the aorta, which is mostly caused by trauma.

As to the aortic dissection, when a tunica intima of the aorta is locally torn, high-pressure blood flow impacts the blood vessel wall, thus a tunica media is torn (the tunica media usually ruptures at an interface between inner ⅓ and outer ⅔ of the tunica media), such that an intact aorta wall structure is bisected, and a dissection lumen is formed in a gap between inner and outer walls of the dissection. In order to be distinguished from the aortic lumen, the dissection lumen is called as a false lumen, and the aortic lumen is called as a true lumen.

Both the aortic aneurysm and the aortic dissection are extremely dangerous diseases, with a mortality rate of greater than 50% within 48 hours after attack, and a mortality rate of greater than 85% within two weeks after attack, thus seriously threatening health of human beings. With the trend of aging in China, a morbidity thereof is constantly rising.

According to Stanford classification, the aortic dissection may be classified into type A dissection and type B dissection.

Type A: a tunica intima tear is located at ascending aorta, aortic arch or proximal descending aorta, and propagation involves ascending aorta or aortic arch, and also may extend to descending aorta and even abdominal aorta.

Type B: a tunica intima tear is usually located at aortic isthmus, and propagation merely involves descending aorta or extends to abdominal aorta, but does not involve ascending aorta or aortic arch.

According to DeBakey classification, the aortic dissection may be classified into type I dissection, type II dissection, and type III dissection.

Type I: a tunica intima tear is located at ascending aorta, and propagation involves abdominal aorta.

Type II: a tunica intima tear is located at ascending aorta, and propagation merely involves ascending aorta.

Type III: a tunica intima tear is located at aortic isthmus, and propagation involves descending aorta (IIIa) or reaches abdominal aorta (IIIb).

Type A is equivalent to type I and type II, occupying about 65%~70% of the aortic dissection; type B is equivalent to type III, occupying about 30%~35% of the aortic dissection.

At present, surgical treatment for such diseases mainly include conventional open surgical operation and minimal invasive endovascular graft exclusion.

The surgical operation treatment is difficult in operating, hard in handling, long in operating time, quite traumatic to patients, and high in mortality rate. Meanwhile, assistant technologies are also needed: deep hypothermia and circulatory arrest, cerebral perfusion, routine extracorporeal circulation, temperature increasing and decreasing, cardiovascular anesthesia and so on. Moreover, within a surgical field, there are many tubes in complex sequences, and numerous anastomotic stomas, thus the time of operation is prolonged, and the time of cerebral ischemia and the time for extracorporeal circulation are also correspondingly prolonged, as a result, the operative mortality and occurrence of complications (particularly cerebral complications) are increased.

In the technology of minimal invasive interventional treatment using an endovascular exclusion principle, a covered stent is usually used to isolate blood and aortic aneurysm or aortic dissection. The covered stents for aortic dissection currently available in the market are mainly made of a metal wire and a PET (polyethylene glycol terephthalate) membrane or ePTFE (polytetrafluoroethylene) membrane covered thereon. The metal wire is fabricated into a cylindrical stent skeleton, with the PET membrane or the ePTFE membrane covered thereon. The covered stent in a compressed state is guided, by a delivery system having a relatively small tube diameter, into a human body along a guide wire implanted in advance, and is accurately released after being delivered to a position of a lesion vessel with the aid of a developing system, to cover a lesion blood vessel segment, and isolate the lesion and form a new blood flow path.

For aneurysm, after blood supply is lost, blood left in an aneurysm cavity gradually forms thrombosis and is muscularized to form vascular tissues. The aneurysm wall in an expansion state shrinks under a negative pressure, and gradually recovers an original state, so as to achieve an object of treating aneurysm. For the aortic dissection, the covered stent covers the tear of the aortic dissection, thrombosis is gradually formed inside the false lumen, and the negative pressure is decreased gradually, thus achieving the object of treating the aortic dissection.

Although the current minimal invasive interventional treatment technique has characteristics of being simple in operation, rapid in effect, and so on, there are still following risks: proximal segments of the covered stents available in the market are poor in plasticity, and have a certain elastic force for straightening the covered stent, thus it is easy to cause appearance of a new dissection tear at the proximal end of the covered stents, and lead to retrograde type A dissection. In the retrograde type A dissection, stem induction is the most important factor.

SUMMARY

The present disclosure provides a plastic covered stent for aortic dissection, which has good flexibility and good radial support strength, and meanwhile has plasticity adapted to aortic dissection lesion.

A plastic covered stent for aortic dissection includes a tubular membrane and multiple annular stents sequentially sutured on the membrane along an axial direction. Part of the annular stents on the membrane are semi-suture stents, and each semi-suture stent has non-suture zones separable from the membrane. When the plastic covered stent is bent, the membrane corresponding to the non-suture zones at an inner bending side of the plastic covered stent is separated from the semi-suture stents and folded inwardly.

The plastic covered stent for aortic dissection according to the present disclosure is delivered through a delivery catheter in an interventional treatment manner to a lesion position of thoracic aortic dissection, and the covered stent is released in the true lumen, thus achieving treatment objects of blocking a dissection tear, reducing a pressure inside the false lumen, and promoting thrombosis inside the false lumen.

The plastic covered stent for aortic dissection is a self-expanding stent. In a natural state, the plastic covered stent for aortic dissection is in a straight-tube shape. When the plastic covered stent for aortic dissection is bent under an external force, at the inner bending side, the annular stents get close to each other, and the membrane corresponding to the non-suture zones is gathered together and folded. Since no suture pulls the annular stents and the membrane in the non-suture zones, foldability of bending flexibility of the membrane is greatly improved, the stents in the non-suture zones are sequentially stacked, and they can get closer to each and overlap. On the basis of the folding of the membrane, and the stacking of the non-suture zones with each other, after the external force is removed, the form of the bending support structure of the covered stent still can be maintained, the flexibility of the covered stent for maintaining the bending form is improved, and plasticity of an external form of the covered stent is achieved.

In the bending state, when the external force is applied to enable the covered stent to restore the straight-tube shape, the covered stent restores and maintains the straight-tube shape.

A number of annular stents are sequentially sutured along the axial direction of the membrane, or a number of annular stents are sutured in a local area of the membrane along the axial direction. A linking structure besides the membrane may be present among the annular stents, or the annular stents are completely independent from each other.

After the covered stent is implanted, only a certain axial area is bent. In order to maintain structural stability of other areas, preferably, the semi-suture stents are distributed at a bending portion of the plastic covered stent for aortic dissection after being implanted.

The semi-suture stent refers to a stent which is not sutured partially, rather than being sutured just in a half area.

In order to maintain the bending form of the covered stent, preferably, the semi-suture stents form at least two adjacent circles. For example, the semi-suture stents form three or four or five or six adjacent circles.

Preferably, the semi-suture stent fluctuates along the axial direction to form a wave while extending circumferentially, and the non-suture zones are located at turning portions of the wave.

Preferably, in two adjacent semi-suture stents, the turning portions pointing to a same direction are aligned with each other.

Each semi-suture stent is in a wave shape, and contains a number of peaks and valleys distributed sequentially at intervals along the circumferential direction. In two adjacent semi-suture stents, the peaks are aligned with each other, and the valleys are aligned with each other.

Preferably, all non-suture zones of each semi-suture stent are located at the turning portions pointing to a same direction. By "pointing to a same direction", it means that crests of waves point to a same direction, that is, the peaks or the valleys point to a same direction.

All non-suture zones of each semi-suture stent are located at the peaks, or all non-suture zones of each semi-suture stent are located at the valleys.

In order to ensure that each semi-suture stent does not shift in position along the axial direction of the membrane, preferably, the non-suture zones of each semi-suture located at the turning portions pointing to a same direction are arranged at intervals.

The non-suture zones may be arranged to be spaced by one or more turning portions pointing to the same direction. Taking that the non-suture zones are arranged at the peaks as an example, the non-suture zones are arranged to be spaced by one or more peaks.

Preferably, the non-suture zones of two adjacent semi-suture stents are in a staggered arrangement in a circumferential direction. Taking that the non-suture zones are arranged at the peaks as an example, the non-suture zones are arranged to be spaced by one peak, and in two adjacent semi-suture stents, a non-suture peak of one semi-suture stent is aligned with a suture peak of the other semi-suture stent along the axial direction of the covered stent.

Preferably, along a trend of a blood vessel, after the plastic covered stent for aortic dissection is implanted, the turning portions pointing to heart are peaks, the turning portions facing away from the heart are valleys, and each annular stent includes connecting rods each connecting one peak and one valley adjacent to the peak.

In order to ensure smooth blood flow, preferably, the non-suture zones of each semi-suture stent are all located at the peaks. When the non-suture zones are located at the peaks, in the bending state, the membrane at the non-suture zones is folded, and a folding edge formed by the folding is adapted to a direction of the blood flow.

Preferably, the peaks of each semi-suture stent are in an alternate arrangement of high and low peaks at intervals according to different axial positions, and the non-suture zones are located at the high peaks. That is, high and low peaks of each semi-suture stent are sequentially distributed at intervals along the circumferential direction, and axial positions of the valleys may be flush or not.

Preferably, the valleys of each semi-suture stent are in an alternate arrangement of deep and shallow valleys at intervals according to different axial positions, and the non-suture zones are located at the deep valleys. That is, deep and shallow valleys of each semi-suture stent are sequentially distributed at intervals along the circumferential direction, and axial positions of the peaks may be flush or not.

Preferably, an axial height of the non-suture zone is $\frac{1}{4}$-$\frac{3}{4}$ of an axial height of the semi-suture stent.

The axial height refers to an axial distance from a highest peak to a lowest valley. Taking that the non-suture zone is located at the peak as an example, for each non-suture zone, the non-suture zone is at a place from the peak to $\frac{1}{4}$-$\frac{3}{4}$ of the axial height of the semi-suture stent.

In order to satisfy special requirements of different blood vessels, the plastic covered stent for aortic dissection according to the present disclosure may be in a tubular shape extending with unequal diameters, for example, the plastic covered stent for aortic dissection is in a tapered-tube shape, or the plastic covered stent for aortic dissection is in a structure with variable diameters constituted by a tapered-tube shape and a straight-tube shape.

In order to realize the tubular structure extending with unequal diameters for the plastic covered stent for aortic dissection, the annular stents in the present disclosure may have different structures.

The plastic covered stent for aortic dissection according to the present disclosure has at least one full-suture annular stent at a proximal end, and also has at least one full-suture annular stent at a distal end. By "full-suture", it means that the peaks and the valleys of the annular stent are all sutured with the membrane.

The present disclosure further provides an aortic dissection stent which includes a covered stent and a bare stent butted with each other, and the covered stent is the plastic covered stent for aortic dissection as mentioned above.

The covered stent is operable to block a proximal tear of the type B dissection, reduce a pressure inside a false lumen, and promote thrombosis inside the false lumen. The bare stent is placed at a distal end of the covered stent, and operable to rebuild a true lumen of the blood vessel, and ensure smooth arterial blood flow in various internal organs.

Butted portions of the covered stent and the bare stent are nested with each other, that is, at least one portion is an overlapping area. An axial length of the overlapping area is set as required.

For the plastic covered stent for aortic dissection according to the present disclosure, when the covered stent is bent, the non-suture zones of two adjacent annular stents located at the inner bending side can be stacked, and the membrane at the non-suture zones is folded towards inside of the covered stent, thus maintaining the bending form of the covered stent.

DETAILED DESCRIPTION

Below the present disclosure is described in detail in combination with the accompanying drawings and embodiments. In the text, a proximal end refers to an end close to a position of heart, and a distal end refers to an end away from the position of heart. In schematic views of the embodiments, an upper side is the proximal end, and a lower side is the distal end.

Embodiment 1

Figure 1:
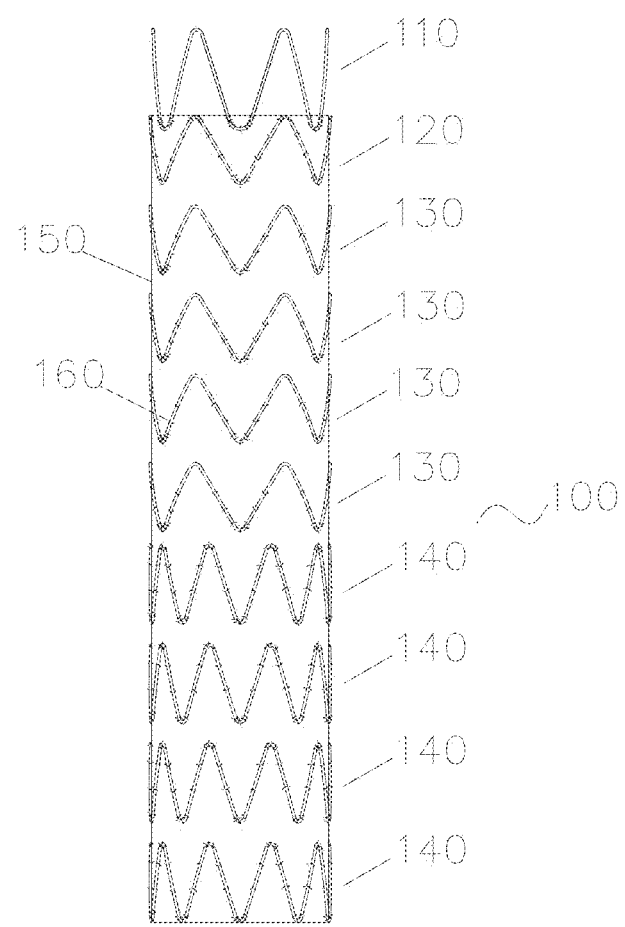
FIG. 1 is a schematic view illustrating a plastic covered stent for aortic dissection according to an embodiment 1.

As illustrated in FIG. 1, a covered stent 100 according to the present embodiment is constituted by a tubular membrane 150 and multiple independent annular stents sequentially sutured on the membrane 150 along an axial direction, namely, an annular stent 110 (a fourth type of annular stent), an annular stent 120 (a first type of annular stent), annular stents 130 (a second type of annular stent), and annular stents 140 (a third type of annular stent), from a proximal end of the covered stent 100 to a distal end of the covered stent 100.

The number of each type of annular stent depends on an axial length of the covered stent 100. In the present embodiment, the number of the annular stent 110 is one, the number of the annular stent 120 is one, the number of the annular stents 130 is four, and the number of the annular stents 140 is four.

The membrane 150 is made of polyester cloth. The membrane 150 on the whole is in a straight cylindrical shape. Each annular stent is sutured on the membrane 150 by a suture 160 to form the covered stent 100.

Each annular stent fluctuates along the axial direction to form a wave while extending circumferentially. Each annular stent is in a closed annular shape in a circumferential direction. In each annular stent, each peak is connected to an adjacent valley by a connecting rod. Based on different axial positions of the annular stents, the annular stents are slightly different in structures.

The annular stent 110 is close to the proximal end of the covered stent. The annular stent 110 has a biggest degree of axial fluctuation. Valleys of the annular stent 110 are sutured with the membrane 150 by the suture 160, with a suture height ranging from 3 mm to 5 mm.

A degree of axial fluctuation of the annular stent 120 is smaller than that of the annular stent 110. The annular stent 110 and the annular stent 120 have a same number of peaks and a same number of valleys. The annular stent 120 is located at the proximal end of the membrane 150. The peaks of the annular stent 120 are flush with an axial end of the membrane 150, meanwhile, the peaks of the annular stent 120 and the peaks of the annular stent 110 are aligned along the axial direction. The peaks, the valleys, and the connecting rods of the annular stent 120 are all sutured with the membrane 150 by the suture 160.

Figure 3A:
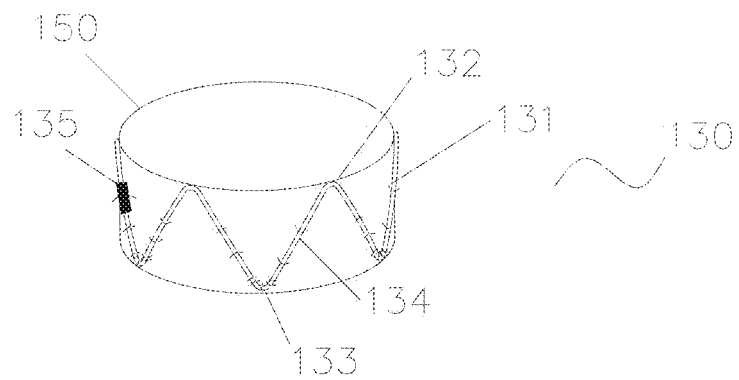
FIG. 3a is a structural schematic view illustrating a second type of annular stent according to the embodiment 1.

As illustrated in FIG. 1, the four annular stents 130 have a same shape as the annular stent 120. The annular stents 130 are arranged at equal intervals along the axial direction of the covered stent, and the peaks of each annular stent 130 are aligned along the axial direction. The annular stents 130 are semi-suture stents, and a state that the annular stent 130 is sutured with the membrane 150 is illustrated in FIG. 3a.

A degree of axial fluctuation of each annular stent 140 is slightly bigger than that of the annular stent 130. The number of the peaks of the annular stent 140 is more than that of the annular stent 130, and the number of the valleys of the annular stent 140 is more than that of the annular stent 130. The four annular stents 140 are arranged at equal intervals along the axial direction of the covered stent. The four annular stents 140 are located at the distal end of the covered stent, and are sutured with the membrane 150 by the suture 160.

Figure 2A:
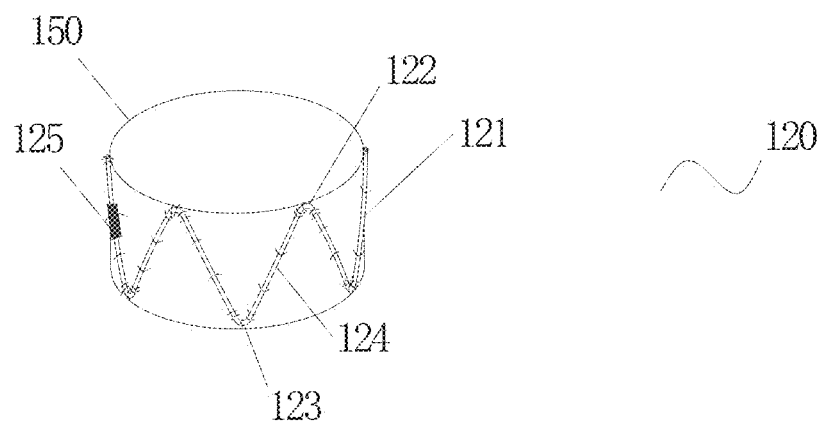
FIG. 2a is a schematic view illustrating a first type of annular stent of the plastic covered stent for aortic dissection according to the embodiment 1.

As illustrated in FIG. 2a, the annular stent 120 is consisted of multiple Z-shape waves, each Z-shape wave includes a peak 122, a valley 123 adjacent to the peak 122, and a connecting rod 124 connected between the peak 122 and the valley 123.

The annular stent 120 is formed by weaving a hyper-elastic nickel-iron alloy wire 121. The hyper-elastic nickel-iron alloy wire 121 may have a wire diameter (i.e. diameter) ranging from 0.3 mm to 0.55 mm. The wire diameter selected in the present embodiment is 0.5 mm.

The annular stent 120 has an axial height that ranges from 10 mm to 18 mm, that is, an axial distance from a highest point of the peak to a lowest point of the valley ranges from 10 mm to 18 mm. In the present embodiment, the annular stent 120 has the axial height of 14 mm.

As illustrated in FIG. 2a, the annular stent 120 has a connecting steel jacket 125 thereon, two ends of the hyper-elastic nickel-iron alloy wire 121 are located inside the connecting steel jacket 125, and the two ends of the nickel-iron alloy wire are fixed inside the steel jacket 125 in a mechanical compressing manner or a welding manner.

Figure 2B:
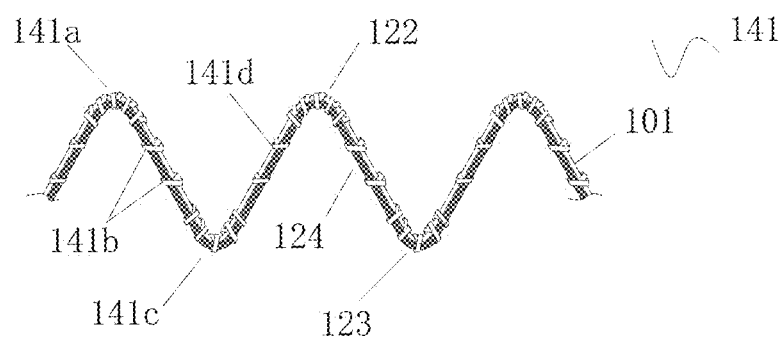
FIG. 2b is a schematic view illustrating suturing of the first type of annular stent according to the embodiment 1.

The annular stent 120 is connected to the membrane 150 in a suturing manner as illustrated in FIG. 2b. The suture 101 accompanies the whole annular stent 120 along the wave shape of the annular stent 120. The annular stent 120 is sutured on the membrane 150 by the suture 101 through a number of suture knots 141d distributed at unequal intervals. The suture 101 has a diameter ranging from 0.05 mm to 0.25 mm. In the present embodiment, the suture 101 has a diameter of 0.1 mm.

As illustrated in FIG. 2b, a suture point 141a is located at the peak 122, and the suture point 141a is consisted of five suture knots 141d arranged uniformly, with each two adjacent suture knots 141d defining an interval ranging from 0.3 mm to 0.8 mm.

A suture point 141b is located on the connecting rod 124 arranged between the peak 122 and the valley 123. The suture point 141b is consisted of two suture knots 141d, and the two suture knots 141d are uniformly distributed on the connecting rod 124. A suture point 141c is located at the valley 123, and is consisted of five suture knots 141d arranged uniformly, with each two adjacent suture knots 141d defining an interval ranging from 0.3 mm to 0.8 mm.

As illustrated in FIG. 3a, a material, a wave shape structure, and a fabricating process of the annular stent 130 are the same as those of the annular stent 120. Each annular stent 130 is consisted of multiple Z-shape waves, and each Z-shape wave includes a peak 132, a valley 133 adjacent to the peak 132, and a connecting rod 134 connected between the peak 132 and the valley 133. Each annular stent 130 is formed by weaving a hyper-elastic nickel-iron alloy wire 131, and two ends of the hyper-elastic nickel-iron alloy wire 131 are fixed by a steel jacket 135. An area where all the annular stents 130 are located constitutes a proximal end main body segment of the covered stent 100.

Figure 3B:
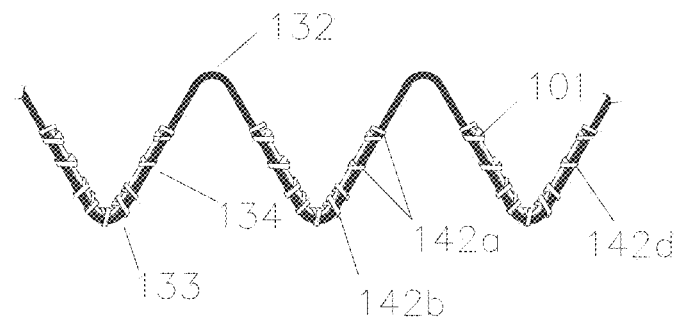
FIG. 3b is a schematic view illustrating suturing of the second type of annular stent according to the embodiment 1.

As illustrated in FIG. 3b, the annular stent 130 is connected to the membrane 150 in a semi-suture manner. The peaks 132 of the annular stent 130 have no suture point. A suture point 142a is located at the connecting rod 134, and is consisted of two suture knots 142d. A suture point 142b is located at the valley 133, and is consisted of five suture knots 142d uniformly arranged, with each two adjacent suture knots 142d defining an interval ranging from 0.3 mm to 0.8 mm.

Each suture unit includes one suture point 142b and two suture points 142a, in a V-shape structure on the whole, and the number of the suture units is the same as that of the valleys of the annular stent 130.

Figure 4:
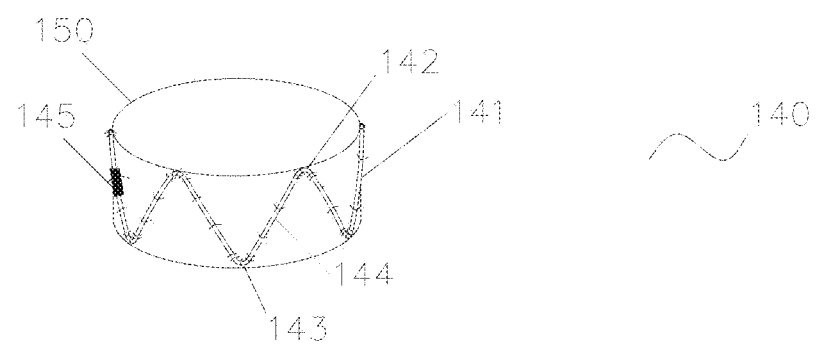
FIG. 4 is a structural schematic view illustrating a third type of annular stent according to the embodiment 1.

As illustrated in FIG. 4, in the present embodiment, the annular stents 140 are located at a distal end segment of the covered stent 100. A material and a fabricating process of each annular stent 140 are the same as those of the annular stent 120. Each annular stent 140 is consisted of multiple Z-shape waves, and each Z-shape wave includes a peak 142, a valley 143 adjacent to the peak 142, and a connecting rod 144 connected between the peak 142 and the valley 143. Each annular stent 140 is formed by weaving a hyper-elastic nickel-iron alloy wire 141, and two ends of the hyper-elastic nickel-iron alloy wire 141 are fixed by a steel jacket 145. A manner of suturing the annular stent 140 and the membrane 150 is the same as that of suturing the annular stent 120 and the membrane 150.

Intervals between the annular stent 120, the annular stents 130, and the annular stents 140 on the membrane 150 range from 3 mm to 5 mm. Actual intervals are appropriately adjusted according to a total axial length of the membrane 150 in a process of suturing the annular stents.

In the present embodiment, a material, a wave shape structure (except an axial height of the wave shape), and a fabricating process of the annular stent 110 are the same as those of the annular stent 120.

Figure 5:
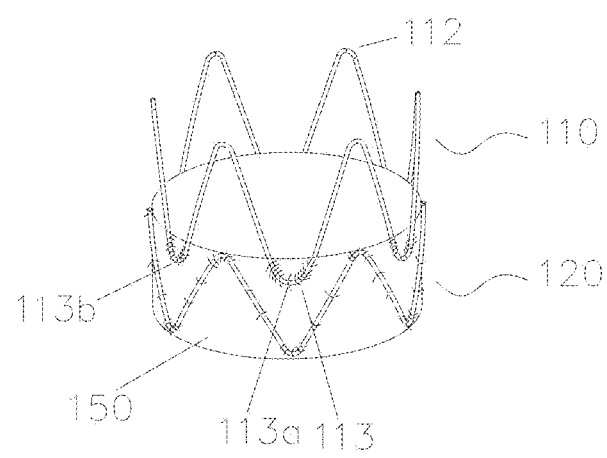
FIG. 5 is a schematic view illustrating a connection between a fourth type of annular stent (bare stent) and a starting end of a membrane according to the embodiment 1.

A manner of suturing the annular stent 110 and the membrane 150 is illustrated in FIG. 5. From a valley bottom 113a of the valley 113 to a position above the valley 113 with a distance ranging from 3 mm to 8 mm, the annular stent 110 is sutured with the proximal end of the membrane 150. A suture point 113b is consisted of five suture knots uniformly arranged, with each two adjacent suture knots defining an interval ranging from 0.3 mm to 0.8 mm.

Figure 10:
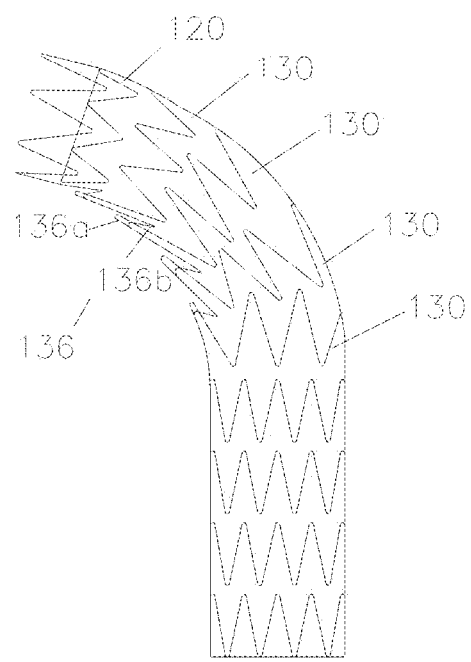
FIG. 10 is a schematic view illustrating plasticity of the covered stent according to the embodiment 1.

As illustrated in FIG. 10, the proximal end main body segment of the covered stent 100 according to the present embodiment has good plasticity, and when the covered stent 100 is bent, adjacent annular stents 130 get close to each other at an inner bending side, and since the peaks of the annular stents 130 facing the proximal end of the covered stent are not sutured, the membrane 150 at the peaks is separated from the annular stents 130 to form a folding portion 136b, and the peaks 136a separating from the membrane 150 may get closer to each other as there is no obstruction of the membrane 150, a bending state of the covered stent 100 can be maintained, and the plasticity of the covered stent 100 in the folding process can be ensured.

Embodiment 2

Figure 6:
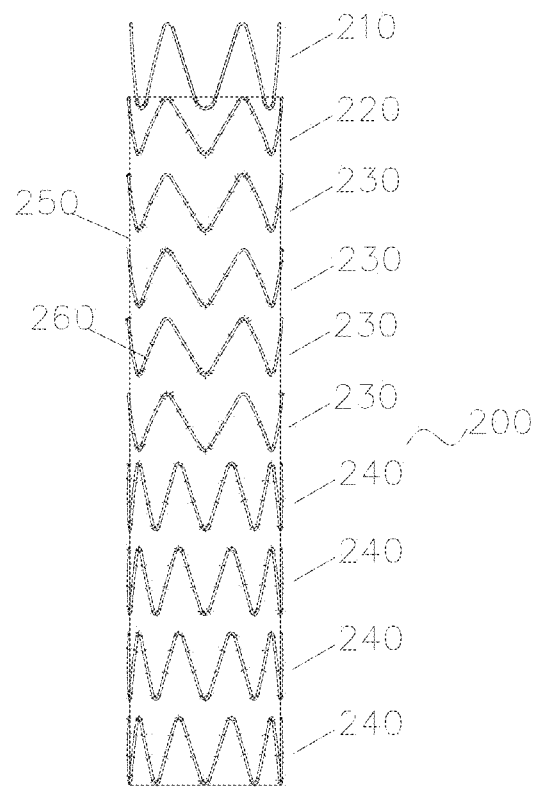
FIG. 6 is a schematic view illustrating a plastic covered stent for aortic dissection according to an embodiment 2.

As illustrated in FIG. 6, a covered stent 200 according to the present embodiment is formed by suturing an annular stent 210, an annular stent 220, annular stents 230 and annular stents 240 on a membrane 250 by sutures 260.

The present embodiment is distinguished from the embodiment 1 merely in that the annular stents 230 and the membrane 250 are sutured in a different manner. A material, a wave shape structure, and a fabricating process of each annular stent 230 are the same as those of the annular stent 120.

Figure 7A:
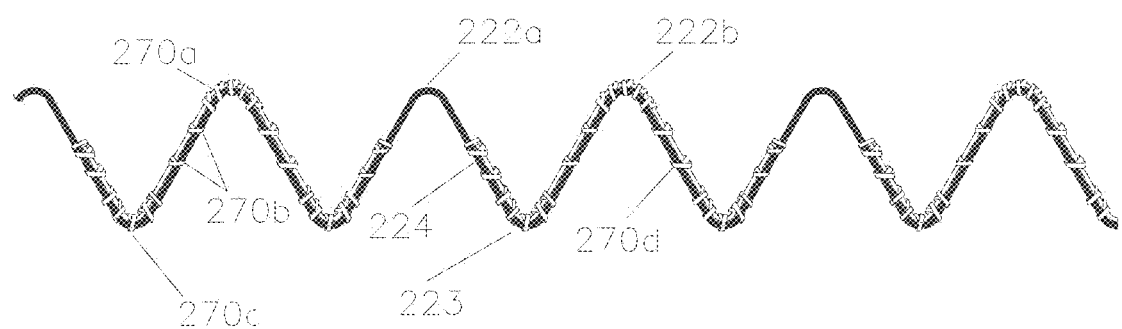
FIG. 7a is a schematic view illustrating suturing of a second type of annular stent according to the embodiment 2.
Figure 7B:
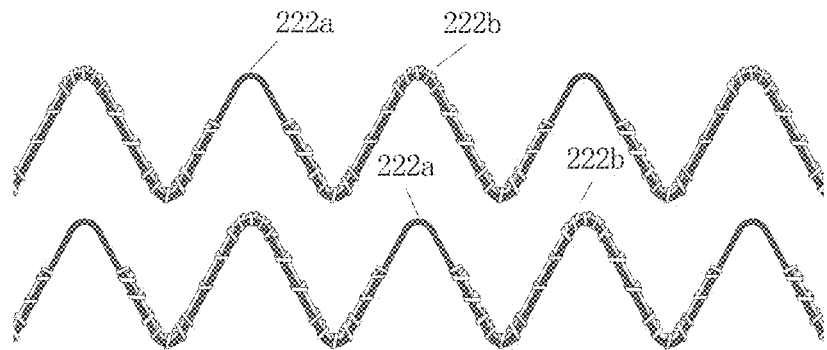
FIG. 7b is a schematic view illustrating an arrangement of two adjacent semi-suture stents that are the second type of annular stent according to the embodiment 2.

A manner of suturing the annular stent 230 and the membrane 250 is illustrated in FIG. 7a. In each annular stent 230, for a peak 222a and a peak 222b adjacent to the peak 222a, the peak 222b has a suture point, and the peak 222a has no suture point. As illustrated in FIG. 7h, viewing from the whole covered stent, the peaks 222b having the suture points and the peaks 222a having no suture point are in an alternate arrangement along a circumferential direction of the membrane.

A suture point 270a located at the peak 222b is consisted of five suture knots 270d, and the five suture knots 270d are arranged uniformly at the peak 222b, with each two adjacent suture knots 270d defining an interval ranging from 0.3 mm to 0.8 mm. A suture point 270b is located on the connecting rod 224. The suture point 270b is consisted of two suture knots 270d, and the two suture knots 270d are uniformly arranged on the connecting rod 224. A suture point 270c is located at the valley 223. The suture point 270c is consisted of five suture knots 270d, and the five suture knots 270d are uniformly arranged at the valley 223, with each two adjacent suture knots 270d defining an interval ranging from 0.3 mm to 0.8 mm.

Embodiment 3

Figure 8:
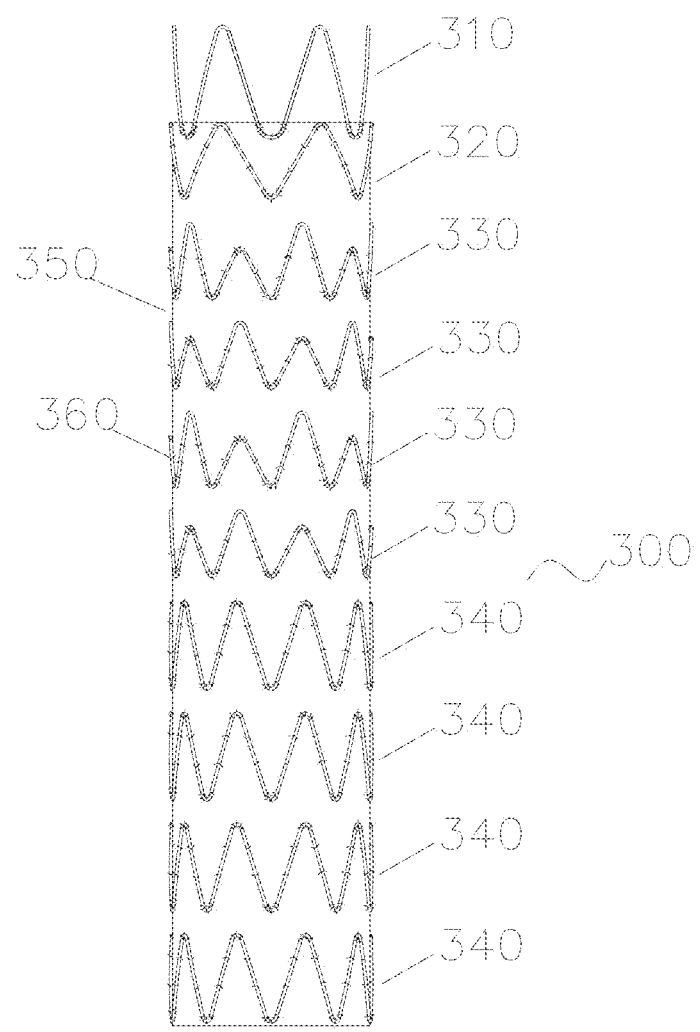
FIG. 8 is a schematic view illustrating a plastic covered stent for aortic dissection according to an embodiment 3.

As illustrated in FIG. 8, a covered stent 300 according to the present embodiment is formed by suturing an annular stent 310, an annular stent 320, annular stents 330, and annular stents 340 on a membrane 350 by sutures 360.

The present embodiment is distinguished from the embodiment 2 merely in that the annular stent 330 is different from the annular stent 230 in structures.

Figure 9A:
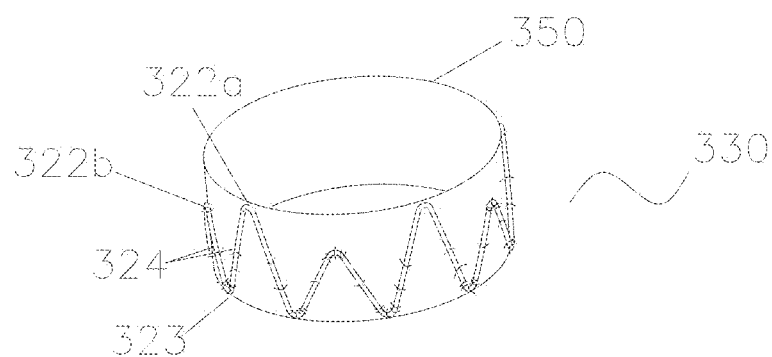
FIG. 9a is a schematic structural view illustrating the second type of annular stent according to the embodiment 3.

As illustrated in FIG. 9a, a material and a fabricating process of each annular stent 330 is the same as those of the annular stent 230, and the distinction merely lies in different wave shape structures, and there is a height difference between two adjacent peaks 322a and 322b of each annular stent 330.

Figure 9B:
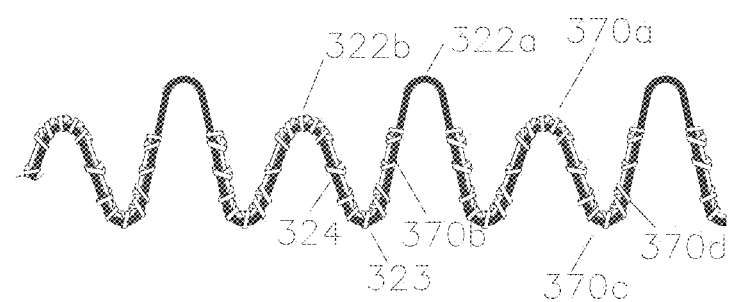
FIG. 9b is a schematic view illustrating suturing of the second type of annular stent according to the embodiment 3.
Figure 9C:
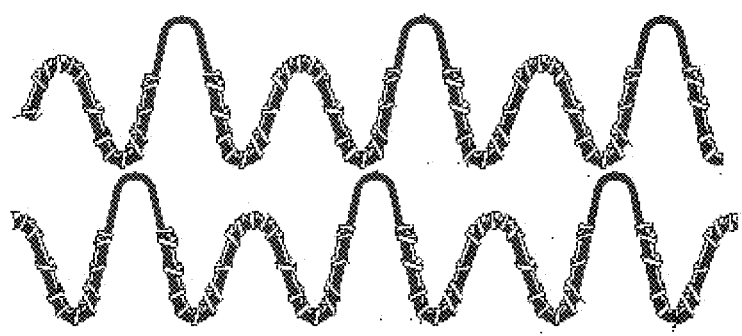
FIG. 9c is a schematic view illustrating suturing of the second type of annular stent according to the embodiment 3.

A manner of suturing the annular stent 330 and the membrane 350 is illustrated in FIG. 9b. There is no suture point at a relatively high peak 322a, and there is a suture point 370a at a relatively low peak 322b. As illustrated in FIG. 9c, viewing from the whole annular stents 330, the peaks 322a and the peaks 322b are in an alternate arrangement along a circumferential direction of the membrane.

The suture pint 370a locating at the peak 322b is consisted of five suture knots 370d, and the five suture knots 370d are uniformly arranged at the peak 322a, with each two adjacent suture knots 370d defining an interval ranging from 0.3 mm to 0.8 mm. A suture point 370b is located on the connecting rod 324. The suture point 370b is consisted of two suture knots 370d, and the two suture knots 370d are uniformly distributed on the connecting rod 324.

A suture point 370c is located at the valley 323. The suture point 370c is consisted of five suture knots 370d, and the five suture knots 370d are uniformly arranged at the valley 323, with each two adjacent suture knots 370d defining an interval ranging from 0.3 mm to 0.8 mm.

Embodiment 4

Figure 11:
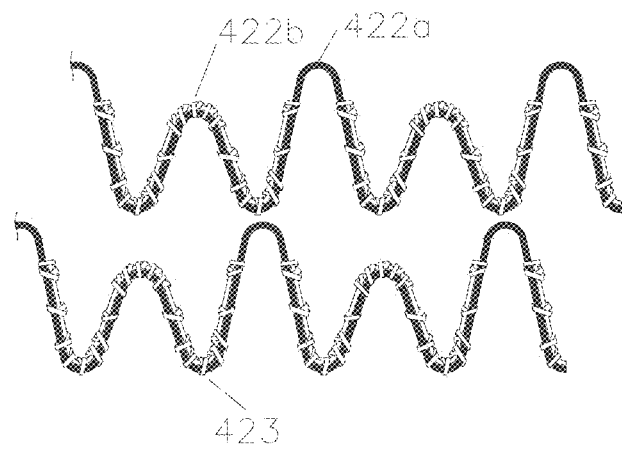
FIG. 11 is a schematic view illustrating an arrangement of two adjacent semi-suture stents that are a second type of annular stent according to an embodiment 4.

As illustrated in FIG. 11, the present embodiment is distinguished from the embodiment 3 merely in that two adjacent semi-suture stents are arranged in a different manner.

As illustrated in FIG. 11, in each semi-suture stent, there is a height difference between each two adjacent peaks 422a and 422b, lowest positions of valleys 423 are flush along the circumferential direction, and in two adjacent semi-suture stents, the peaks of one semi-suture stent and the valleys of the other semi-suture stent are aligned in axial positions.

What is claimed is:

1. A plastic covered stent for aortic dissection, comprising:
    a tubular membrane; and
    a plurality of annular stents sequentially sutured on the tubular membrane along an axial direction, wherein annular stents on a part of the tubular membrane are semi-suture stents, each of the semi-suture stents has non-suture zones separable from the part of the tubular membrane, and when the plastic covered stent for aortic dissection is bent, the part of the tubular membrane corresponding to the non-suture zones of each of the semi-suture stents at an inner bending side of the plastic covered stent for aortic dissection is separated from each of the semi-suture stents and folded,
    wherein each of the semi-suture stents fluctuates along the axial direction to form a wave while extending circumferentially, the non-suture zones of each of the semi-suture stents are located at turning portions of the wave, the non-suture zones of two adjacent semi-suture stents are in a staggered arrangement in a circumferential direction, and two closest non-suture zones in the circumferential direction of a single semi-suture stent located at the turning portions pointing to a first direction are separated by sutures at at least one other turning portion pointing to the first direction and two turning portions pointing to a second direction,
    wherein along a trend of a blood vessel, the turning portions pointing to a heart are peaks, the turning portions facing away from the heart are valleys, and each of the annular stents comprises connecting rods each connecting one peak and one valley adjacent to the peak.

2. The plastic covered stent for aortic dissection of claim 1, wherein the semi-suture stents are distributed at a bending portion of the plastic covered stent for aortic dissection.

3. The plastic covered stent for aortic dissection of claim 1, wherein the semi-suture stents form at least two circles.

4. The plastic covered stent for aortic dissection of claim 1, wherein all the non-suture zones of each of the semi-suture stents are located at the turning portions pointing to a same direction.

5. The plastic covered stent for aortic dissection of claim 1, wherein the non-suture zones of each of the semi-suture stents located at the turning portions pointing to a same direction are arranged at intervals.

6. The plastic covered stent for aortic dissection of claim 1, wherein the non-suture zones of each of the semi-suture stents are all located at the peaks.

7. The plastic covered stent for aortic dissection of claim 1, wherein the peaks of each of the semi-suture stents are in an alternate arrangement of high peaks and low peaks at intervals according to different axial positions, and the non-suture zones of each of the semi-suture stents are located at the high peaks.

8. The plastic covered stent for aortic dissection of claim 1, wherein the valleys of each of the semi-suture stents are in an alternate arrangement of deep valleys and shallow valleys at intervals according to different axial positions, and the non-suture zones of each of the semi-suture stents are located at the deep valleys.

9. The plastic covered stent for aortic dissection of claim 1, wherein a ratio of an axial height of each of the non-suture zones of each of the semi-suture stents to an axial height of each of the semi-suture stents ranges from ¼ to ¾.

10. An aortic dissection stent, comprising:
a bare stent; and
a covered stent butted with the bare stent and comprising:
   a tubular membrane; and
   a plurality of annular stents sequentially sutured on the tubular membrane along an axial direction, wherein annular stents on a part of the tubular membrane are semi-suture stents, each of the semi-suture stents has non-suture zones separable from the part of the tubular membrane, and when the covered stent for aortic dissection is bent, the part of the tubular membrane corresponding to the non-suture zones of each of the semi-suture stents at an inner bending side of the covered stent for aortic dissection is separated from each of the semi-suture stents and folded,
wherein each of the semi-suture stents fluctuates along the axial direction to form a wave while extending circumferentially, the non-suture zones of each of the semi-suture stents are located at turning portions of the wave, the non-suture zones of two adjacent semi-suture stents are in a staggered arrangement in a circumferential direction, and two closest non-suture zones in the circumferential direction of a single semi-suture stent located at the turning portions pointing to a first direction are separated by sutures at at least one other turning portion pointing to the first direction and two turning portions pointing to a second direction,
wherein along a trend of a blood vessel, the turning portions pointing to heart are peaks, the turning portions facing away from the heart are valleys, and each of the annular stents comprises connecting rods each connecting one peak and one valley adjacent to the peak.

11. The aortic dissection stent of claim 10, wherein the peaks of each of the semi-suture stents are in an alternate arrangement of high peaks and low peaks at intervals according to different axial positions, and the non-suture zones of each of the semi-suture stents are located at the high peaks.

12. The aortic dissection stent of claim 10, wherein the valleys of each of the semi-suture stents are in an alternate arrangement of deep valleys and shallow valleys at intervals according to different axial positions, and the non-suture zones of each of the semi-suture stents are located at the deep valleys.

* * * * *